(12) United States Patent
Booth

(10) Patent No.: US 8,062,284 B2
(45) Date of Patent: Nov. 22, 2011

(54) CATHETER ASSEMBLY WITH AN ADJUSTABLE LOOP

(75) Inventor: Norman Booth, Wattle Grove (AU)

(73) Assignee: Cathrx Ltd, Homebush Bay, NSW (AU)

( * ) Notice: Subject to any disclaimer, the term of this patent is extended or adjusted under 35 U.S.C. 154(b) by 462 days.

(21) Appl. No.: 10/587,534

(22) PCT Filed: Jan. 20, 2005

(86) PCT No.: PCT/AU2005/000058
§ 371 (c)(1), (2), (4) Date: Sep. 12, 2007

(87) PCT Pub. No.: WO2005/070491
PCT Pub. Date: Aug. 4, 2005

(65) Prior Publication Data
US 2008/0255539 A1    Oct. 16, 2008

Related U.S. Application Data

(60) Provisional application No. 60/539,519, filed on Jan. 26, 2004.

(51) Int. Cl.
*A61M 25/00* (2006.01)

(52) U.S. Cl. ........ 604/528; 604/523; 604/524; 604/525; 604/526; 604/527; 604/530; 604/531; 604/532

(58) Field of Classification Search .......... 604/158–161, 604/164.1, 164.09, 164.12, 164.13, 523–528, 604/530–532; 600/374, 434, 435
See application file for complete search history.

(56) References Cited

U.S. PATENT DOCUMENTS

| | | | |
|---|---|---|---|
| 4,101,984 A | 7/1978 | MacGregor | |
| 5,269,810 A | 12/1993 | Hull et al. | |
| 5,522,874 A | 6/1996 | Gates | |
| 5,556,380 A * | 9/1996 | Ridinger et al. | 604/540 |
| 5,643,281 A * | 7/1997 | Suhocki et al. | 606/113 |
| 5,738,683 A | 4/1998 | Osypka | |

(Continued)

FOREIGN PATENT DOCUMENTS

CN    1234281 A    11/1999

(Continued)

OTHER PUBLICATIONS

Supplementary Partial European Search Report mailed on Feb. 12, 2007, for EP Application No. 01977995 filed on Oct. 19, 2001, five pages.

(Continued)

*Primary Examiner* — Theodore Stigell
*Assistant Examiner* — Larry R Wilson
(74) *Attorney, Agent, or Firm* — TraskBritt

(57) ABSTRACT

A catheter assembly including at least one introducer defining a passage receiving an elongate tubular member having a proximal end, a distal end, and a lumen extending between an elongate shape-imparting element received in the lumen and imparting a predetermined shape to the distal end of the elongate tubular member, when the distal end of the elongate tubular member is extended beyond a distal end of the at least one introducer. A distal end of the one-piece shape-imparting element extends from the lumen of the elongate tubular member and is anchored proximal the distal end of the at least one introducer.

16 Claims, 2 Drawing Sheets

U.S. PATENT DOCUMENTS

| | | | |
|---|---|---|---|
| 5,834,051 A | 11/1998 | Woloszko et al. | |
| 5,931,862 A | 8/1999 | Carson | |
| 6,014,579 A | 1/2000 | Pomeranz et al. | |
| 6,071,274 A * | 6/2000 | Thompson et al. | 604/528 |
| 6,071,278 A | 6/2000 | Panescu et al. | |
| 6,231,570 B1 | 5/2001 | Tu et al. | |
| 6,254,598 B1 | 7/2001 | Edwards et al. | |
| 6,322,559 B1 * | 11/2001 | Daulton et al. | 606/41 |
| 6,517,551 B1 | 2/2003 | Driskill | |
| 6,607,505 B1 | 8/2003 | Thompson | |
| 6,607,520 B2 * | 8/2003 | Keane | 606/2 |
| 7,178,234 B2 | 2/2007 | Kawasaki et al. | |
| 2001/0007070 A1 * | 7/2001 | Stewart et al. | 606/41 |
| 2002/0173815 A1 | 11/2002 | Hogendijk et al. | |
| 2003/0013985 A1 * | 1/2003 | Saadat | 600/549 |
| 2003/0014037 A1 | 1/2003 | Thompson | |
| 2006/0089634 A1 * | 4/2006 | Anderson et al. | 606/41 |

FOREIGN PATENT DOCUMENTS

| | | | |
|---|---|---|---|
| EP | 0 479 435 A2 | 9/1991 | |
| EP | 0 479 435 A3 | 9/1991 | |
| EP | 479435 A2 * | 4/1992 | |
| EP | 0479435 A2 * | 8/1992 | |
| EP | 0 937 481 A1 | 8/1999 | |
| WO | WO-90/08466 A1 | 8/1990 | |
| WO | WO-94/12098 A1 | 6/1994 | |
| WO | WO-94/21167 A1 | 9/1994 | |
| WO | WO-96/36860 A2 | 11/1996 | |
| WO | WO-96/36860 A3 | 11/1996 | |
| WO | WO-00/12012 A1 | 3/2000 | |
| WO | 02/32497 A1 | 4/2002 | |

OTHER PUBLICATIONS

International Search Report issued for PCT Application No. PCT/AU2005/000058 mailed Mar. 10, 2005, five pages.

International Search Report issued for PCT Application No. PCT/AU2005/000058 mailed Mar. 10, 2005, five pages.

Japanese Office Action mailed on Apr. 27, 2010, for JP Application No. 2006-549778, filed on Jan. 20, 2005, English Translation, three pages.

Supplementary Partial European Search Report mailed on Apr. 16, 2010, for EP Application No. 05700090, 2 pages.

* cited by examiner

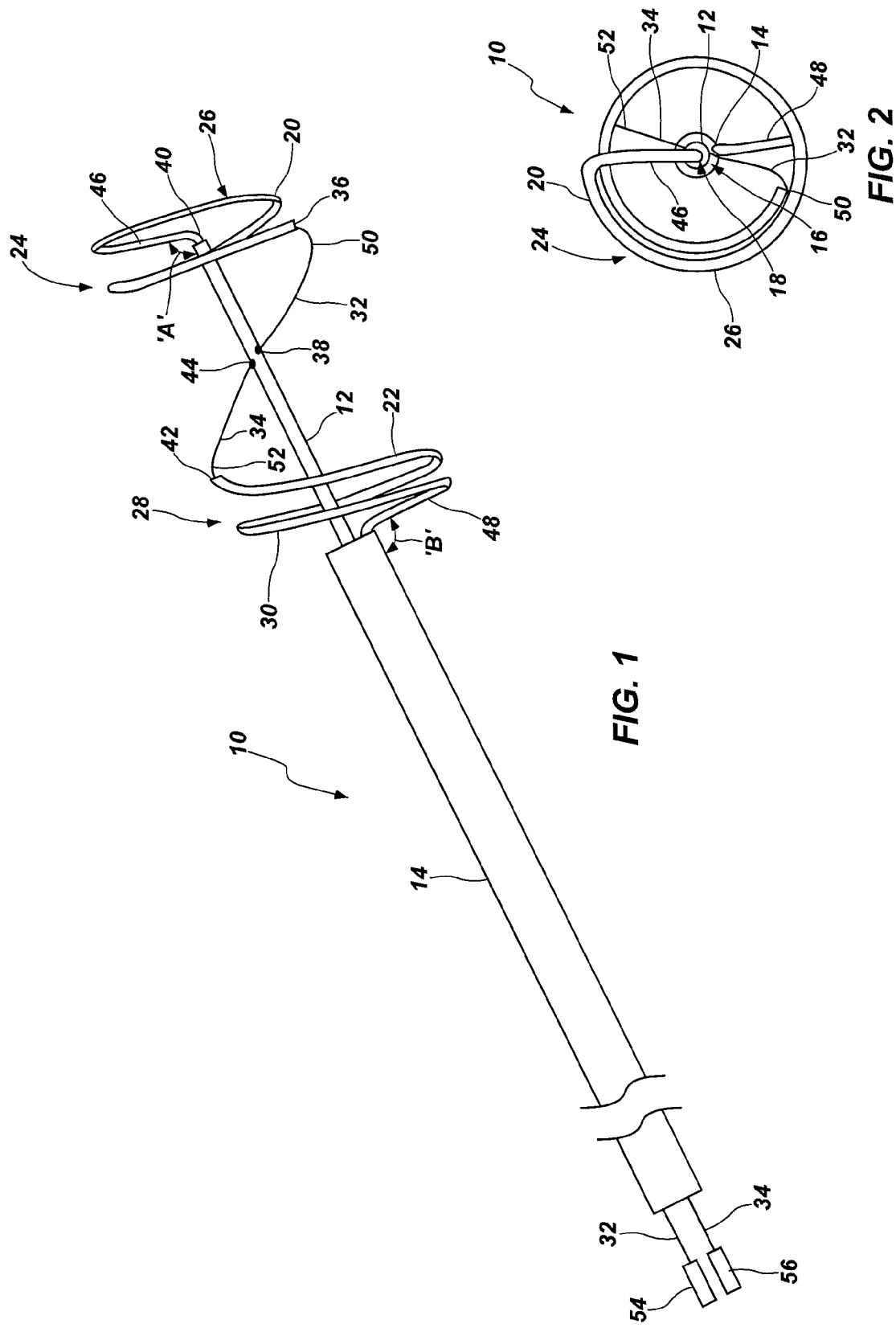

CATHETER ASSEMBLY WITH AN ADJUSTABLE LOOP

CROSS-REFERENCE TO RELATED APPLICATIONS

The present application is a National Phase filing under 35 U.S.C. §371 of International Application No. PCT/AU2005/000058 filed on 20 Jan. 2005, which claims priority to U.S. Provisional Patent Application No. 60/539,519 filed on 26 Jan. 2004, the contents of which are incorporated herein by reference in their entirety.

FIELD OF THE INVENTION

This invention relates to a catheter system. More particularly, the invention relates to a catheter assembly with an adjustable loop.

BACKGROUND OF THE INVENTION

Catheter systems are becoming an increasingly common way of diagnosing and treating abnormal heart conditions, in particular, heart arrhythmias. Such arrhythmias can be treated with drugs or by use of electronic devices such as pacemakers. However, neither of these treatments cures the problem but only alleviates it.

In contrast, the use of ablative techniques has been shown to cure arrhythmias. Thus, catheters having mapping electrodes and/or ablative electrodes are inserted through the vascular system of a patient's body so that a distal end of the catheter can be placed accurately in the relevant chamber of the heart. For the treatment of atrial fibrillation, the distal end is placed at or around the ostium of one or more of the pulmonary veins, in turn, to effect ablation.

In still other applications for ablative catheters, the catheter may need to be placed against a wall of a blood vessel or organ, for example, in heating tumors for treatment of such tumors. It is therefore desirable that a distal end of the catheter be substantially planar so that the distal end of the catheter assembly can be placed in contact with the wall of the vessel or organ.

SUMMARY OF THE INVENTION

According to a first aspect of the invention, there is provided a catheter assembly, which includes:

at least one introducer, the at least one introducer defining at least one passage;

an elongate tubular member slidably received within the at least one passage of the at least one introducer, the tubular member having a proximal end and a distal end and at least one lumen extending between the proximal end and the distal end; and an elongate, shape-imparting element received in the at least one lumen of the tubular member, the shape-imparting element imparting a predetermined shape to the distal end of the tubular member when the distal end of the tubular member is extended beyond a distal end of the introducer, a distal end of the shape-imparting element extending from the at least one lumen of the tubular member and being anchored proximally a distal end of the introducer.

A proximal end of the shape-imparting element may be connectable to a control mechanism which, in use, applies torsion to the shape-imparting element to effect adjustment of the predetermined shape of the distal end of the tubular member. The predetermined shape imparted to the distal end of the tubular member may be a loop formation.

Thus, the tubular member may form a cranked arm when it is extended from its introducer, the cranked arm being arranged transversely with respect to a longitudinal axis of the introducer and the cranked arm leading into a spiral shape forming the loop formation. The spiral shape may circumscribe at least 360° and, preferably, about 540° so that, when a loop formation of maximum diameter is formed, there are electrodes arranged substantially all the way around the loop formation.

The cranked arm may extend from the end of the introducer at an included angle of about, or exceeding, 90° to facilitate the formation of a substantially planar loop formation at the distal end of the introducer.

Preferably, the assembly includes at least two introducers, each introducer having a tubular member associated with it.

Thus, a first introducer may be received within a passage of a second introducer, a second tubular member, associated with the second introducer, being slidably received within the passage of the second introducer.

Once again, the second tubular member may be carried on a shape-imparting element received within a lumen of the second tubular member so that the second tubular member is able to be formed into a second predetermined shape, preferably also a loop formation when the second tubular member is extended from the second introducer.

The shape-imparting element associated with the second tubular member, i.e., the second shape-imparting element, may extend beyond a distal end of the second tubular member. A distal end of the second shape-imparting element may be anchored distally with respect to the distal end of the second tubular member, but proximally with respect to the distal end of the first introducer. An anchor point of the first shape-imparting element may be in register with an anchor point of the second shape-imparting element. Both anchor points may be arranged on the first introducer.

The first introducer and the second introducer may be in the form of sleeves into which the first tubular member and the second tubular member, respectively, are withdrawn to be introduced into a patient's body. When the catheter assembly is at the desired location in the patient's body, the first tubular member and the second tubular member may be extended relative to their respective introducers to form the first loop formation and the second loop formation, respectively.

Each tubular member may be manufactured in accordance with the Applicant's manufacturing technique as disclosed in PCT Publication No. WO 02/32497, entitled "An Electrical Lead," the contents of which are incorporated herein by reference. The benefit of this manufacturing technique is that an unimpeded lumen is provided with conductors for the electrodes being at least partially embedded in a wall of a tubular member. Hence, a catheter assembly of small diametrical dimensions can be formed, thereby facilitating steering of the catheter assembly through the vascular system of a patient's body.

Each shape-imparting element may be in the form of a shape memory alloy wire such as a Nitinol wire, which is in its superelastic state.

The proximal end of each wire may terminate in an actuating mechanism. Conveniently, each actuating mechanism may be connected to an appropriate control member of a control handle of the catheter assembly to facilitate imparting torsion to each wire. It will be appreciated that, when torsion is imparted to the wire, the cranked arm rotates about the longitudinal axis of the catheter assembly increasing or decreasing the size of the loop formation bearing in mind that the distal end of the wire is anchored.

According to a second aspect of the invention, there is provided a catheter assembly, which includes:

at least one introducer, the at least one introducer defining a passage;

an elongate, tubular member slidably received within the passage of the at least one introducer, the tubular member having a proximal end and a distal end and a lumen extending between the proximal end and the distal end; and an elongate, shape-imparting element received in the lumen of the tubular member, a distal end of the shape-imparting element extending beyond a distal end of the tubular member and being anchored proximally a distal end of the introducer, the arrangement being such that, when a distal portion of the tubular member is extended beyond the distal end of the introducer, the shape-imparting element imparts, to the distal portion of the tubular member, a cranked arm portion extending transversely relative to a longitudinal axis of the introducer and a loop formation supported on the arm portion so that torsion imparted to a proximal end of the shape-imparting element causes rotation of the arm portion about the longitudinal axis of the introducer to effect adjustment of a diameter of the loop formation of the distal portion of the tubular member.

BRIEF DESCRIPTION OF THE DRAWINGS

An embodiment of the invention is now described by way of example with reference to the accompanying drawings in which:

FIG. 1 shows a schematic, side view of a catheter assembly, in accordance with an embodiment of the invention;

FIG. 2 shows a schematic, end view of the catheter assembly; and

DETAILED DESCRIPTION OF EXEMPLARY EMBODIMENT

Figure 3:
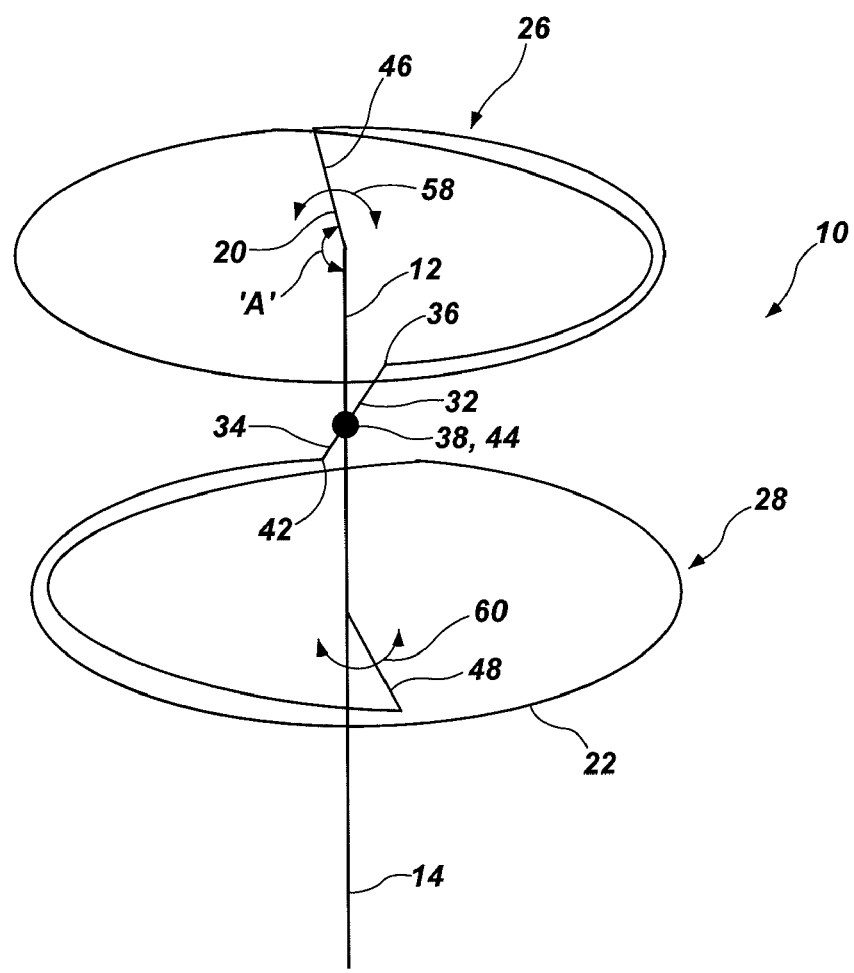
FIG. 3 shows a schematic, three-dimensional view of the catheter assembly.

In the drawings, reference numeral 10 generally designates a catheter assembly, in accordance with an embodiment of the invention.

The catheter assembly 10 includes a first introducer in the form of a first sleeve 12 received within a passage 16 of a second introducer, also in the form of a second sleeve 14. The first sleeve 12 defines a passage 18.

A first elongate tubular member 20 is slidably received within the passage 18 of the first sleeve 12. Similarly, a second tubular member 22 is slidably received within the passage 16 of the second sleeve 14. Each tubular member 20, 22 is manufactured in accordance with the Applicant's manufacturing technique, as disclosed in PCT Publication No. WO 02/32497 entitled "An Electrical Lead". As indicated earlier in this specification, the contents of that earlier patent application are incorporated herein by reference.

While not shown in the drawings, a plurality of electrodes are arranged at spaced intervals along the tubular members 20, 22. The electrodes on the tubular members 20 and 22 can be used for sensing, ablation and/or heating purposes.

As illustrated, a distal portion 24 of the tubular member 20 is formed into a loop formation 26 when the tubular member 20 is extended from the first sleeve 12. Similarly, a distal portion 28 of the tubular member 22 is formed into a loop formation 30 when the tubular member 22 is extended from the second sleeve 14.

As described in the Applicant's International Patent Publication No. WO 03/094764, dated 9 May 2003, and entitled "An Ablation Catheter," the contents of which are also incorporated herein by reference, electrodes on the loop formation 26 may, typically, be used for sensing of electrical activity in walls of a patient's vascular system with the loop formation 30 being used for ablation purposes and being arranged, in use, at an ostium of the relevant pulmonary vein.

However, there are applications where it is desired to place the loop formation 26 against a wall of a patient's organ, for example, for heat treating tumors. In that application, it is desirable that the loop formation 26 lies in a plane with no protuberances arranged distally of that plane. This is also advantageous when it is desired to steer the catheter assembly 10 through a patient's vascular system. It will be appreciated that any protuberances distally of the distal end 40 of the first sleeve 12 could snag on a wall of the patient's vein or artery as the catheter assembly 10 is being steered, resulting in difficulty in steering the catheter assembly 10, and possible damage to the patient's vascular system.

To form the loop formations 26 and 30 in the tubular members 20 and 22, respectively, each formation of the tubular members 20, 22 has an elongate shape-imparting element 32, 34 respectively, extending through the lumen of the tubular members 20, 22.

Each shape-imparting element or wire 32, 34 is in the form of a length of shape memory alloy wire such as a Nitinol wire.

The wire 32 protrudes beyond a distal end 36 of the tubular member 20. A distal end 38 of the wire 32 extends back toward a proximal end of the catheter assembly 10 and is anchored on the first sleeve 12 proximally of a distal end 40 of the first sleeve 12.

The wire 34 protrudes beyond a distal end 42 of the tubular member 22. A distal end 44 of the wire 34 is anchored to the first sleeve 12 approximately in register with the distal end 38 of the wire 32.

With this arrangement, the loop formation 26 formed at the distal end of the catheter assembly 10 when the tubular member 20 is extended from the first sleeve 12 lies substantially in a plane extending transversely to a longitudinal axis of the catheter assembly 10.

The wire 32 is preformed so that, when the tubular member 20 is extended beyond the distal end 40 of the first sleeve 12, the loop formation 26 is formed. The loop formation 26 is supported on a cranked arm portion 46. The cranked arm portion 46 projects from the distal end 40 of the tubular member 20 with an included angle 'A' (FIG. 3) exceeding 90°. This facilitates the formation of a substantially planar loop formation 26. Similarly, when the tubular member 22 is extended from the second sleeve 14, the wire 34 imparts the loop formation 30 to the distal portion of the tubular member 22. Once again, the loop formation 30 is supported on a cranked arm portion 48. As is the case with the cranked arm portion 46 of the loop formation 26, the cranked arm portion 48 projects from the second sleeve 14 with an included angle 'B' (FIG. 1) exceeding 90°. Once again, this facilitates the formation of a substantially planar loop formation 30.

Each loop formation 26, 30 is in the form of a spiral circumscribing at least 360° and, preferably, about 540°. This ensures that, when a loop formation 26, 30 of maximum diameter is formed, electrodes are arranged substantially all the way around the relevant loop formation 26, 30.

The portion of the wire 32 projecting beyond the distal end 36 of the tubular member 20 forms a bend 50 which is not covered by the tubular member 20. The bend 50 facilitates retraction of the tubular member 20 into the first sleeve 12 and the wire 32 lies substantially flush with an external surface of the first sleeve 12. Hence, a compact, small diameter arrangement is formed by the first sleeve 12 and its associated tubular member 20. Similarly, the wire 34 projecting beyond the distal end 42 of the tubular member 22 is cranked relative to the tubular member 22 to form a bend 52. Once again, this facilitates retraction of the tubular member 22 into the second sleeve 14 and facilitates the wire 34 lying flush against the outer surface of the tubular member 12. As with the case of the tubular member 20 and its first sleeve 12, a compact, smaller diameter arrangement of second sleeve 14 and tubular member 22 is provided.

A proximal end of the wire 32 terminates in an actuating mechanism or actuator 54. Similarly, a proximal end of the wire 34 terminates in an actuating mechanism or actuator 56. The actuators 54, 56 are connected to a loop control mechanism (not shown) of a handle (also not shown) of the catheter assembly 10. For example, the loop control mechanism may be a thumb wheel for each wire 32 or it may be an electrically activated device.

By means of the control mechanism, torsion is imparted to each of the wires 32, 34. When torsion is imparted to the wire 32, the cranked arm portion 46 of the tubular member 20 is caused to rotate about the longitudinal axis of the catheter assembly 10, as indicated schematically by arrows 58 in FIG. 3 of the drawings. In so doing, the diameter of the loop formation 26 can be increased or decreased as desired. Similarly, by imparting torsion to the wire 34, the cranked arm portion 48 of the tubular member 22 is caused to rotate about the longitudinal axis of the catheter assembly 10, as indicated schematically by arrows 60. Once again, this facilitates increasing or decreasing the diameter of the loop formation 30, as desired.

It is, accordingly, an advantage of the invention that a catheter assembly 10 with adjustable loop formations or loops 26, 30 is formed. The absence of any distal support members for supporting the loops 26,30 or driving the loops 26, 30 torsionally results in a more compact, smaller diameter catheter assembly 10. This greatly facilitates steering of the catheter assembly 10 through a vascular system of a patient's body. In addition, the fact that no protuberances are required distally of loop formation 26 of the catheter assembly 10 means that the loop formation 26 can be placed in contact with a wall of a patient's vessel or organ to facilitate heat treatment of that vessel or organ, for example, in the treating of tumors. In addition, the absence of any protuberances distally of the distal end of the tubular member 20 of the catheter assembly 10 facilitates steering of the catheter assembly 10 through the vascular system of a patient's body.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A catheter assembly, including:
   at least one introducer having a longitudinal axis, the at least one introducer defining at least one passage;
   an elongate tubular member slidably received within the at least one passage of the at least one introducer, the tubular member having a proximal end and a distal end and at least one lumen extending between the proximal end and the distal end; and
   an elongate, one piece shape-imparting element received in the at least one lumen of the tubular member to extend from the proximal end of the tubular member and the at least one introducer and through the distal end of the tubular member, the one piece shape-imparting element imparting a predetermined shape to the distal end of the tubular member when the distal end of the tubular member is extended beyond a distal end of the at least one introducer, the predetermined shape including a formation in a plane substantially orthogonal to the longitudinal axis of the at least one introducer, a distal end of the one piece shape-imparting element extending beyond the at least one lumen of the tubular member and being anchored proximally a distal end of the introducer at a location external of the at least one introducer, wherein, due, at least in part, to the anchoring of the distal end of the one piece shape-imparting element to the at least one introducer, the formation is adjusted in the plane substantially orthogonal to the longitudinal axis of the at least one introducer in terms of an inner area of the predetermined shape in the plane substantially orthogonal to the longitudinal axis of the at least one introducer, when torsion is applied to the one piece shape-imparting element.

2. The catheter assembly of claim 1, wherein a in which a proximal end of the shape-imparting element is connectable to a control mechanism which, in use, applies torsion to the shape-imparting element to effect adjustment of the predetermined shape of the distal end of the tubular member.

3. The catheter assembly of claim 1, wherein the predetermined shape imparted to the distal end of the tubular member is a loop formation.

4. The catheter assembly of claim 3, wherein the tubular member forms a cranked arm when it is extended from its at least one introducer, the cranked arm being arranged transversely with respect to a longitudinal axis of the at least one introducer and the cranked arm leading into a spiral shape forming the loop formation.

5. The catheter assembly of claim 4, wherein the spiral shape circumscribes at least 360°.

6. The catheter assembly of claim 4, wherein the spiral shape circumscribes about 540°.

7. The catheter assembly of claim 4, wherein the cranked arm extends from the distal end of the at least one introducer at an included angle of about, or exceeding, 90° to facilitate the formation of a substantially planar loop formation at the distal end of the at least one introducer.

8. The catheter assembly of claim 1, further including at least two introducers, each introducer having a tubular member associated with it.

9. The catheter assembly of claim 8, wherein the at least two introducers include a first introducer and a second introducer, the first introducer being received within a passage of the second introducer, a second tubular member, associated with the second introducer, being slidably received within a passage of the second introducer.

10. The catheter assembly of claim 9, wherein the second tubular member is carried on a shape-imparting element received within a lumen of the second tubular member so that the second tubular member is able to be formed into a second predetermined shape when the second tubular member is extended from the second introducer.

11. The catheter assembly of claim 10, wherein the shape-imparting element associated with the second tubular member extends beyond a distal end of the second tubular member.

12. The catheter assembly of claim 11, wherein a distal end of the second shape-imparting element is anchored distally with respect to the distal end of the second tubular member, but proximally with respect to the distal end of the first introducer.

13. The catheter assembly of claim 12, wherein an anchor point of the first shape-imparting element is in register with an anchor point of the second shape-imparting element.

14. The catheter assembly of claim 13, wherein both anchor points are arranged on the first introducer.

15. The catheter assembly of claim 10, wherein each shape-imparting element is in the form of a shape memory alloy wire.

16. A catheter assembly, including:
   at least one introducer defining a passage;
   an elongate, tubular member slidably received within the passage of the at least one introducer, the tubular member having a proximal end and a distal end and a lumen extending between the proximal end and the distal end; and
   an elongate, one piece shape-imparting element received in the lumen of the tubular member to extend from the proximal end of the tubular member and the at least one introducer and through the distal end of the tubular member, a distal end of the one piece shape-imparting element extending beyond a distal end of the tubular member and being anchored proximally a distal end of the at least one introducer at a location external of the at least one introducer, the arrangement being such that, when a distal portion of the tubular member is extended beyond the distal end of the at least one introducer, the one piece shape-imparting element imparts a predetermined shape to the distal portion of the tubular member, the predetermined shape comprising:
   a cranked arm portion extending transversely relative to a longitudinal axis of the at least one introducer; and
   a loop formation supported on the cranked arm portion, the loop formation extending about the longitudinal axis of the at least one introducer, wherein due to the anchoring of the distal end of the one piece shape-imparting element to the at least one introducer, applying torsion to the one piece shape-imparting element effects adjustment of a diameter of the loop formation of the distal portion of the tubular member.

* * * * *